US006287827B1

(12) United States Patent
Li et al.

(10) Patent No.: US 6,287,827 B1
(45) Date of Patent: Sep. 11, 2001

(54) HALO- OR HYDROXY-SUBSTITUTED NOCATHIACIN ANTIBIOTICS

(75) Inventors: Wenying Li, Middletown; John E. Leet, Madison; Kin S. Lam, North Haven, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/562,388

(22) Filed: May 1, 2000

Related U.S. Application Data

(60) Provisional application No. 60/132,550, filed on May 5, 1999.

(51) Int. Cl.⁷ .................................................... C12P 17/00
(52) U.S. Cl. .............................................. 435/117; 435/41
(58) Field of Search ....................................... 435/117, 41

(56) References Cited

U.S. PATENT DOCUMENTS

| | | |
|---|---|---|
| 4,478,831 | 10/1984 | Keller-Juslen et al. . |
| 5,451,581 | 9/1995 | Lee et al. . |

FOREIGN PATENT DOCUMENTS

| | | |
|---|---|---|
| WO 00/03722 | 1/2000 | (WO) . |

OTHER PUBLICATIONS

T. Sasaki, et al, J. of Antibiotics, 51(8), pp. 715–721, 1998.

C. Pascard, et al, J. Am. Chem. Soc., 99(19), pp. 6418–6423, 1977.

F. Benazet, et al, Experientia, 36, pp. 414–416, 1980.

U. Mocek, et al, J. Am. Chem. Soc., 115(17), pp. 7557–7568, 1993.

D. A. Steinberg, et al, J. Antibiotics, 47(8), pp. 887–893, 1994.

P. T. Northcote, et al, J. Antibiotics, 47(8), pp. 894–900, 1994.

P. T. Northcote, et al, J. Antibiotics, 47(8), pp. 901–908, 1994.

M. Lee and R. S. Phillips, "Synthesis and Resolution of 7–Fluorotryptophans," Bioorg. Med. Chem. Lett., 1(9), pp. 477–480, 1991.

E. D. Bergmann and E. Hoffman,, "6–Fluoro–, 6–Methoxy–, and 7–Methoxy–Tryptophan," J. Chem. Soc., pp. 2827–2829, 1962.

D. J. Hook, et al, J. Chromatography, 385, pp. 99–108, 1987.

*Primary Examiner*—Jon P. Weber
*Assistant Examiner*—Brett Ozga
(74) *Attorney, Agent, or Firm*—Samuel J. DuBoff

(57) ABSTRACT

Fermentation of Nocardia sp. ATCC-202099 in the presence of a halogen- or hydroxy-substituted tryptophan precursor yields a novel corresponding halogen- or hydroxy-substituted nocathiacin compound which has broad spectrum antibiotic activity against Gram-positive bacteria and has in vivo efficacy in animals.

7 Claims, 8 Drawing Sheets

HALO- OR HYDROXY-SUBSTITUTED NOCATHIACIN ANTIBIOTICS

This application claims the benefit of U.S. Provisional Application No. 60/132,550, filed May 5, 1999.

BACKGROUND OF THE INVENTION

Multidrug-resistant strains of many clinically important pathogenic bacteria, including methicillin-resistant *Staphylococcus aureus* (MRSA), *Streptococcus pneumoniae*, *Mycobacterium tuberculosis*, and Enterococci strains are becoming a worldwide health problem. There is an urgent need to discover new agents to treat patients infected with multidrug-resistant bacteria. A new group of thiazolyl peptide antibiotics, (designated herein as nocathiacins) having inhibitory activity at the nanomolar level against Gram-positive bacteria has been discovered. The present invention relates to novel antibiotic halo- or hydroxy-substituted nocathiacin compounds, and comprising the process for preparing them by precursor-directed biosynthesis with Nocardia sp. ATCC-202099 or mutants thereof. The novel nocathiacin antibiotics disclosed herein exhibit potent antimicrobial activity against Gram-positive bacteria in vitro, and exhibit in vivo efficacy in a systemic *Staph. aureus* infection model in animals. The nocathiacin compounds are antibiotics useful in the treatment of bacterial infections in humans.

PRIOR ART

The substituted nocathiacin antibiotic compounds of this invention are produced by Nocardia sp. ATCC-202099 in a novel fermentation process. This microorganism also produces nocathiacin I and II, which were previously described by J. E. Leet et al (U.S. Provisional Patent Application Serial No. 60/093,021 filed Jul. 16, 1998) and Sasaki, T. et al, *J. of Antibiotics* 51, No. 8, pp. 715–721 (1998). The nocathiacin antibiotics are related to but clearly distinguishable from nosiheptide (Prange T. et al., *J. Am Chem Soc.* 99, 6418 (1977); Benazet, F. et. al. *Experientia* 36, 414 (1980); Floss, H. G. et al., *J. Am Chem Soc.* 115, 7557 (1993); glycothiohexide-a (Steinberg, D. A. et al, J. Antibiot. 47, 887 (1994); M. D. Lee et al, *J. Antibiot.* 47, 894 (1994); M. D. Lee et al, *J Antibiot.* 47, 901 (1994); U.S. Pat. No. 5,451,581, 1995), and Antibiotic S-54832A (U.S. Pat. No. 4,478,831, 1984). Nocathiacin I (R is OH) and II (R is H) are indicated by the formula

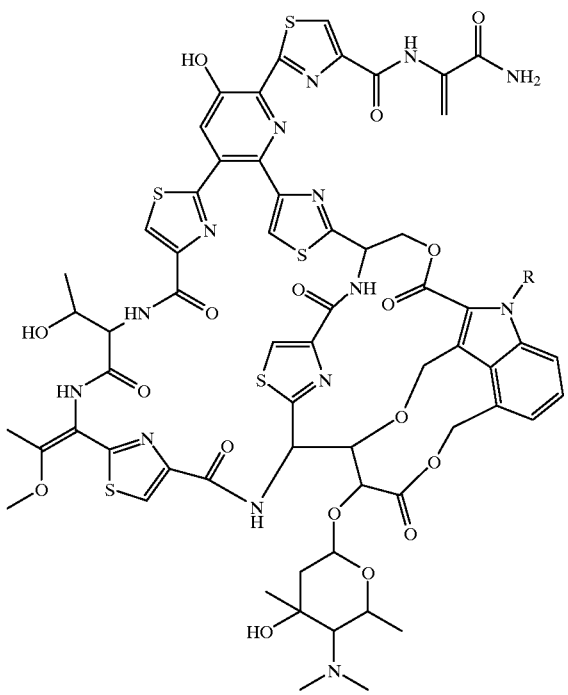

SUMMARY OF THE INVENTION

The invention concerns novel antibiotic compounds of Formula IV, or pharmaceutically acceptable salts thereof, which are halo- or hydroxy-substituted nocathiacins produced by precursor-directed biosynthesis with nocathiacin antibiotic producing microorganisms. Specifically, 5-fluoronocathiacin is obtained by the fermentation of Nocardia sp. ATCC-202099 or mutants thereof, in the presence of 5-fluorotryptophan. The fermentation process is accomplished under submerged aerobic conditions in an aqueous medium containing carbon and nitrogen nutrient at a pH of about 5–8 for a sufficient time to produce 5-fluoronocathiacin. The resulting antibiotics exhibit improved antibiotic activity against a broad spectrum of Gram-positive bacteria, compared to nocathiacin I or II.

The invention also deals with pharmaceutical compositions and methods for treating bacterial infections with the novel nocathiacins, as well as a biologically pure culture Nocardia sp. ATCC-202099 from which the antibiotic is obtained.

The utility of the subject compounds in the treatment of bacterial infections is based upon the expectation that compounds which inhibit Gram-positive bacteria in vitro and in vivo can be used as antibiotics in animals, and in particular, humans. The compounds of this invention were found to have antibiotic activity, particularly in inhibiting the growth of Gram-positive bacteria.

DETAILED DESCRIPTION OF THE INVENTION

Figure 1:
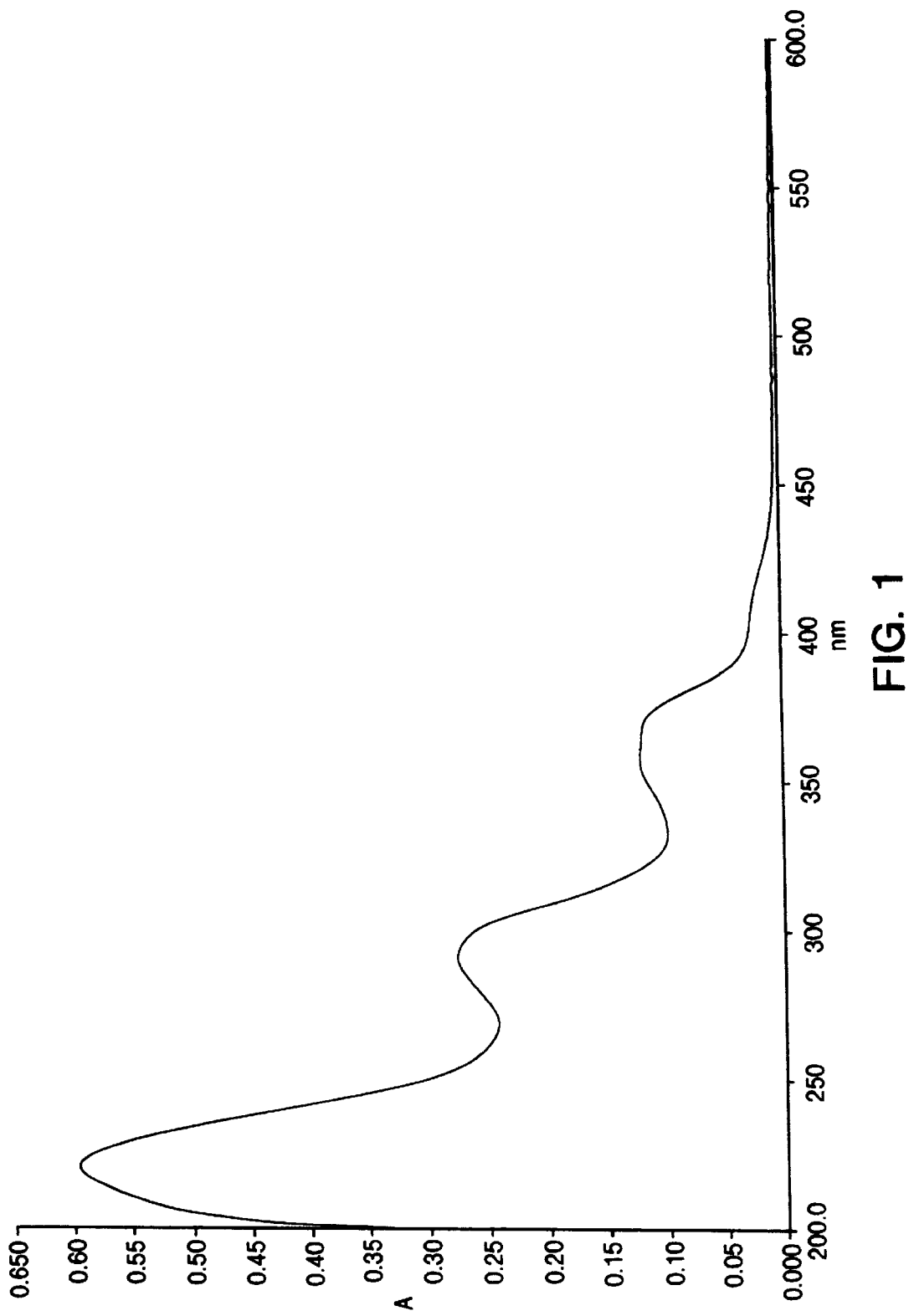
FIG. 1 Shows the ultraviolet absorption (UV) spectrum of 5-fluoronocathiacin.

The present invention describes novel halogen- or hydroxy-substituted nocathiacin antibiotic compound(s) IV obtained through precursor-directed biosynthesis. Halogen means bromine, chlorine, fluorine and iodine. The invention provides an efficient method for the preparation of such substituted nocathiacins. The novel process of this invention comprises fermentation of Nocardia sp. ATCC-202099 or mutants thereof, or other nocathiacin producing microorganisms, in the presence of a halogen- or hydroxy-substituted tryptophan compound(s) III in a nutrient medium, and isolation of the resulting substituted nocathiacin product, in a conventional manner.

The novel nocathiacin compound(s) IV have the formula

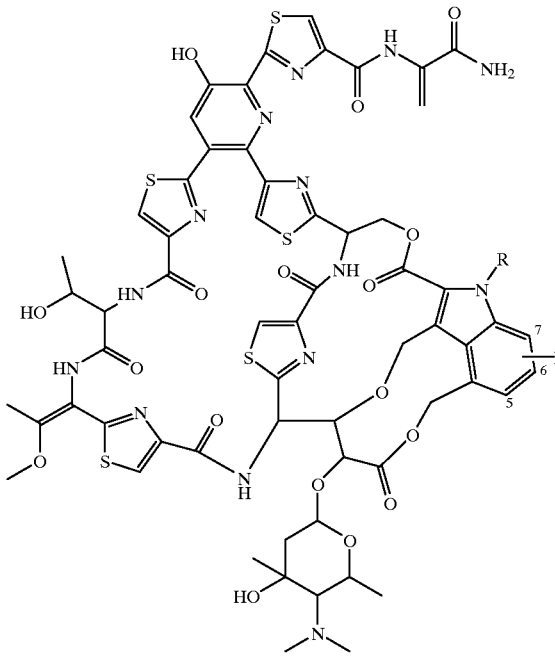

(IV)

wherein:
R is H or OH; and
X is halogen or OH.

Tryptophan is represented by the following formula

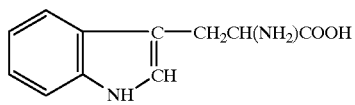

The halogen- or hydroxy-substituted tryptophan precursor compound(s) III used to make the corresponding nocathiacin derivatives herein are represented by the formula

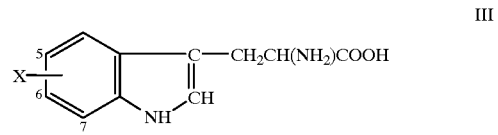

III

The substituted tryptophan compound(s) III can be prepared by procedures well known in the prior art. This is illustrated below in the following two methods for making 5-, 6- or 7-fluorotryptophans.

Method 1 : 5-Fluorotryptophan and 7-fluorotryptophan

Ref: Minsu Lee and Robert S. Phillips, Synthesis and Resolution of 7-Fluorotryptophans, *Bioorg. Med. Chem. Lett.*, 1(9), 477–489, 1991

Fluoroaniline 1 was diazotized and reduced with SnCl$_2$ to give 2, which was added to a mixture of (EtO$_2$C)$_2$CHNHAc, sodium methoxide and H$_2$C=CHCHO in benzene to form 3. Reflux of 3 with dilute sulfuric acid for 5 hours afforded indole 4. Saponification and decarboxylation followed by N-deprotection of 4 yielded fluorotryptophan 5.

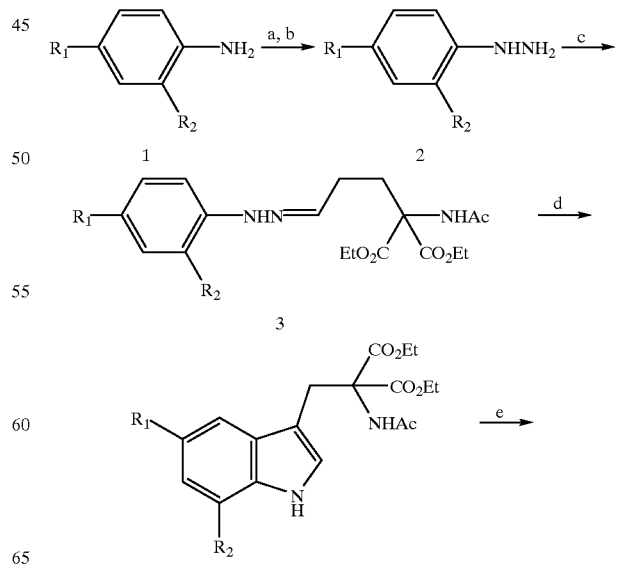

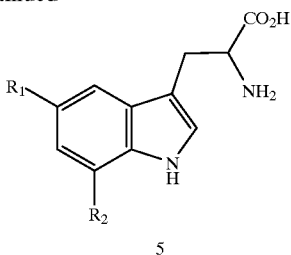

5: 5-fluorotryptophan: $R_1$=F, $R_2$=H; 7-fluorotryptophan: $R_1$=H, $R_2$=F.

a) $NaNO_2/H^+$; b) $SnCl_2$; c) $(EtO_2C)_2CHNHAc/MeO^-/H_2C=CHCHO$; d) $H^+$; e) $OH^-/H^+$

Method 2 : 5-Fluorotryptophan and 6-fluorotryptophan

Ref: Ernst D. Bergmann and Eliahu Hoffmann, 6-Fluoro-, 6-Methoxy-, and 7-Methoxy-tryptophan, *J. Chem. Soc.*, 1962, 2827–2829. Fluoroindole 6 was reacted with a mixture of dioxan, glacial acetic, formalin solution and aqueous 55% dimethylamine solution to give 7. Reflux of 7, $(EtO_2C)_2CHNHCHO$, NaOH and toluene under nitrogen yielded 8, which was treated with sodium hydroxide then glacial acetic acid to afford fluorotryptophan 9.

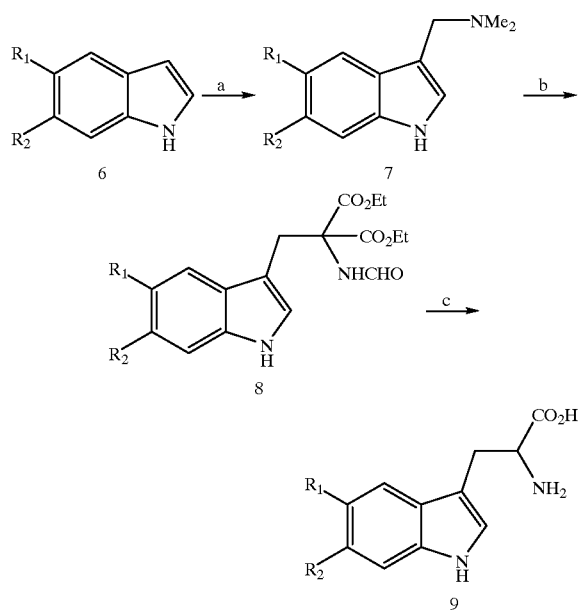

9: 5-fluorotryptophan: $R_1$=F, $R_2$=H; 6-fluorotryptophan: $R_1$=H $R_2$=F.

a) $Me_2NH$, HCHO, HOAc; b) NaOH, $(EtO_2C)_2CHNHCHO$; c) $OH^-/H^+$.

The microorganisms, Nocardia sp. ATCC-202099, employed in the present invention may be any microorganism capable of producing nocathiacin. The microorganism, regardless of origin or purity, may be employed in the free state or immobilized on a support such as by physical adsorption or entrapment. The preferred precursor-directed biosynthesis microorganism that was used in this study for producing the new nocathiacin compound(s) IV was isolated from a soil sample collected in New Mexico. The culture was deposited on Mar. 4, 1998 with the American Type Culture Collection in Rockville, Md. with the accession number of ATCC 202099. The taxonomic analysis of Nocardia sp. ATCC-202099 has been described in U.S. Provisional Patent Application Ser. No. 60/093,021 filed Jul. 16, 1998.

In general, the desired novel substituted nocathiacin compound(s) IV (for example, 5-fluoronocathiacin) can be produced by culturing the aforementioned microorganism in the presence of an appropriate concentration of the corresponding substituted tryptophan precursor compound(s) III, (for example, 5-fluorotryptophan) in an aqueous nutrient medium containing sources of assimilable carbon and nitrogen, preferably under submerged aerobic conditions.

Thus, derivative compound(s) IV of nocathiacin I (where R is OH) can be made using the procedures described herein, by using the appropriately substituted tryptophan precursor compound in the directed biosynthesis reaction. For example, 5-fluorotryptophan can be used to make 5-fluoronocathiacin; 6-hydroxytryptophan can be used to make 6-hydroxynocathiacin; 7-bromotryptophan can be used to make 7-bromonocathiacin, etc. Similarly, derivative(s) IV of nocathiacin II (where R is H) can be made using the corresponding substituted tryptophan precusor compound(s) III.

Using 5-fluoronocathiacin as an example (i.e. where R is OH and X is 5-fluoro), the aqueous medium is incubated at a temperature between 22° C. and 35° C., preferably at 28° C. The aqueous medium is incubated for a period of time necessary to complete the biosynthesis as monitored by high pressure liquid chromatography (HPLC) usually for a period of about 1–5 days after the addition of 5-fluorotryptophan, on a rotary shaker operating at about 180–300 rpm with a throw of about 2 inches.

Growth of the microorganisms may be achieved by one of ordinary skill of the art by the use of appropriate medium. Appropriate media for growing microorganism include those which provide nutrients necessary for the growth of microbial cells. A typical medium for growth includes necessary carbon sources, nitrogen sources, and trace elements. Inducers may also be added. The term inducer as used herein, includes any compound enhancing formation of the desired enzymatic activity within the microbial cell.

Carbon sources may include sugars such as glucose, fructose, galactose, maltose, sucrose, mannitol, sorbital, glycerol starch and the like; organic acids such as sodium acetate, sodium citrate, and the like; and alcohols such as ethanol, propanol and the like.

Nitrogen sources may include N-Z amine A, corn steep liquor, soybean meal, beef extract, yeast extract, tryptone, peptone, cottonseed meal, peanut meal, amino acids such as sodium glutamate and the like, sodium nitrate, ammonium sulfate and the like.

Trace elements may include magnesium, manganese, calcium, cobalt, nickel, iron, sodium and potassium salts. Phosphates may also be added in trace or preferably, greater than trace amounts.

The medium employed may include more than one carbon or nitrogen source or other nutrient. Preferred media for growth include aqueous media, particularly that described in the example herein.

The product, 5-fluoronocathiacin, can be recovered from the culture medium by conventional means which are commonly used for the recovery of other known biologically active substances. Accordingly 5-fluoronocathiacin can be obtained upon extraction of the culture with a conventional solvent, such as ethyl acetate, treatment with a conventional resin (e.g. anion or cation exchange resin, non-ionic adsorption resin), treatment with a conventional adsorbent (e.g.

activated charcoal, silica gel, cellulose, alumina), crystallization, recrystallization, and/or purification by reverse phase preparative HPLC.

Microorganisms and Culture Conditions

The precursor-directed biosynthesis process using Nocardia sp. ATCC-202099 as the producing host is as follows. From the frozen vegetative stock culture of using Nocardia sp. ATCC-202099, 4 ml was used to inoculate 100 ml of seed medium contained the following per liter of deionized water: soluble starch, 20 g; Dextrose, 5 g; N-Z case, 3 g; yeast extract, 2 g; fish meat extract, 5 g; calcium carbonate 3 g, in a 500-ml flask. The culture was incubated at 24–32° C. on a rotary shaker operating at 250 rpm for 3 days. Two to Eight ml of the resulting culture was used to inoculate 100 ml of producing medium consisting of the following per liter of deionized water: HY yeast 412, 10 g; Dextrose, 20 g; Nutrisoy, 10 g, in a 500-ml flask. The producing cultures were incubated at 24–32° C. on a rotary shaker operating at 180–250 rpm for 1 to 3 days. Suitable amount of sterile 5-fluoro-tryptophan aqueous solution (4 to 10 mg/ml) was then added to each flask to reach a final concentration of 0.1 to 1 mg/ml. The cultures were then returned to the shaker and incubated for additional 1 to 5 days at 24–32° C. and 180–250 rpm. The cultures were then processed for the recovery of the 5-fluoronocathiacin.

Isolation and structural characterization

The purification of 5-fluoronocathiacin from Nocardia sp. ATCC-202099 fed with 5-fluorotryptophan was monitored using C18 HPLC-UV, and accomplished by extraction with ethyl acetate and chloroform-methanol 1:1, followed by silica gel chromatography and reverse phase (C18) preparative HPLC. Spectral data indicated 5-fluoronocathiacin, a thiazolyl peptide antibiotic. The structure of 5-fluoronocathiacin, shown below, was assigned based on 2D NMR studies and positive ion electrospray HRMS and MS/MS data.

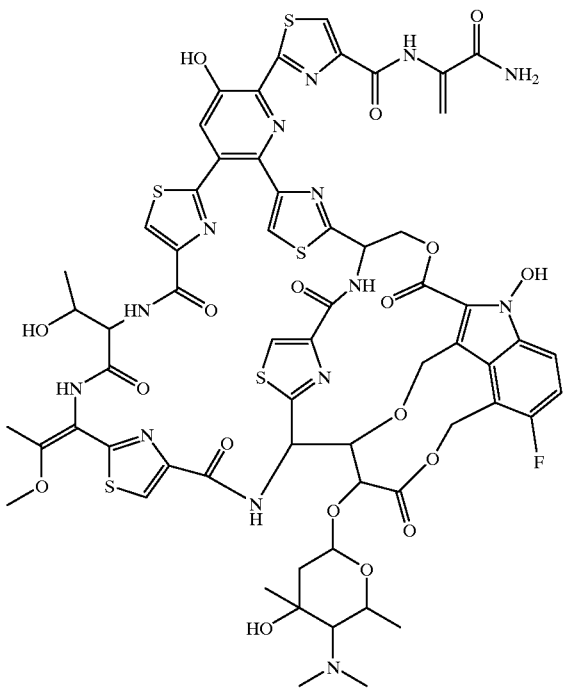

Materials

Hexanes, ethyl acetate, chloroform, methanol, acetonitrile, and tetrahydrofuran (anhydrous HPLC grade) were obtained from EM Science Company. These solvents were not repurified or redistilled. Water used in chromatography experiments refers to in-house deionized water passed through a Millipore 4 cartridge reagent grade water system (10 mega ohm Milli-Q water). Dicalite (diatomaceous earth) was manufactured by Grefco Minerals, Torrance, Calif. LiChroprep Si 60, 25–40 $\mu$m was from EM Separations, N.J., a U.S. associate of E. Merck, Germany.

Analytical Thin Layer Chromatography (TLC)

Uniplate Silica Gel GHLF precoated thin layer chromatography plates (scored 10 x 20 cm, 250 microns) were purchased from Analtech, Inc., Newark, Del. Fractions were spotted using size 2 microliter Microcaps (disposable pipets) and the plates were developed in a tank equilibrated with chloroform-methanol-water (90:10:1 v/v). The components of the resulting chromatogram were visualized by long wavelength UV light and/or ceric sulfate-sulfuric acid spray reagent followed by prolonged heating.

Analytical HPLC

The purification of the 5-fluoronocathiacin was monitored by HPLC analysis on an APEX 5$\mu$ ODS column, 4.6 mm i.d.x15 cm l. (product of Jones Chromatography Inc., Lakewood, Colo). Analyses were done on a Hewlett Packard 1100 Series Liquid Chromatograph, with UV detection at 254 nm. A gradient system of acetonitrile and 0.01M potassium phosphate buffer pH 3.5 was used, according to the method of D. J. Hook et.al. (*I. Chromatogr*. 385, 99 (1987). The eluant was pumped at a flowrate of 1.2 ml/min.

Preparative HPLC

The following components were used to construct a preparative HPLC system: Beckman Instruments Inc. (Somerset, N.J.), Beckman "System Gold" 126 Programmable Solvent Module; Beckman 166 Programmable Detector Module; Beckman "System Gold" Version 711U software; IBM PS/2 55SX System Controller; Preparative HPLC column (reverse phase: C18; YMC Inc. (Wilmington, N.C.) ODS-AQ or Pro-C18, 5$\mu$ particle size, 120 Å pore size, 20 mm i.d.x150 mm l., fitted with a ODS-A 25$\mu$ particle size, 120 Å pore size, 10 mm i.d.x10 mm l. drop-in guard module; mobile phase 0.1M ammonium acetate-tetrahydrofuran isocratic; flow rate 10 ml/min. UV detection: 360 nm.

Analytical Instrumentation

Low resolution MS measurements were performed with a Finnigan SSQ 7000 single quadrupole mass spectrometer, using the positive electrospray ionization mode. MS/MS measurements were conducted in the positive electrospray ionization mode with a Finnigan TSQ 7000 tandem quadrupole mass spectrometer using Argon collision gas or a Finnigan LCQ ion trap mass spectrometer. High resolution MS data were determined with a Finnigan MAT 900 magnetic sector mass spectrometer, positive electrospray ionization mode, ppg reference. The UV spectra were obtained using a Hewlett-Packard 8452A diode array spectrophotometer. IR measurements were taken on a Perkin Elmer 2000 Fourier Transform spectrometer. $^1$H-NMR and $^{13}$C-NMR spectra were obtained on a Bruker DRX-500 instrument operating at 500.13 and 125.76 MHz, respectively, using a Nalorac microprobe. Chemical shifts are reported in ppm relative to solvent (DMSO-d$_6$, $\delta_H$ 2.49; $\delta_C$ 39.6). The $^{19}$F-NMR spectrum was obtained on a Bruker DPX-300 instrument operating at 282 MHz, using a QNP probe; CCl$_3$F external reference. CD data were recorded with a Jasco J-720 spectropolarimeter.

In a similar manner, the other halogen- or hydroxy-substituted nocathiacin compound(s) IV can be made and recovered.

When the nocathiacin compounds herein are employed as pharmaceutical compositions for the treatment of bacterial infections, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The term pharmaceutically acceptable salt includes solvates, hydrates, acid addition salts and quaternary salts. The acid addition salts are formed from a nocathiacin compound having a basic nitrogen and a pharmaceutically acceptable inorganic or organic acid including but not limited to hydrochloric, hydrobromic, sulfuric, phosphoric, methanesulfonic, acetic, citric, malonic, succinic, fumeric, maleic, sulfamic, or tartaric acids. Quaternary salts are formed from a basic nocathiacin compound and an alkyl or arylalkyl halide, preferably methyl or benzyl bromide.

EXAMPLES

The following examples set out the preparation of substituted nocathiacin compound(s) IV by precursor-directed biosynthesis. Reasonable variations, such as those which would occur to a skilled artisan can be made herein without departing from the scope of the invention.

5-FLUORONOCATHIACIN (R IS OH: X IS 5-FLUORO) PREPARED BY PRECURSOR-DIRECTED BIOSYNTHESIS

Biosynthesis

Example 1

From the frozen vegetative stock culture of Nocardia sp. ATCC-202099, 4 ml was used to inoculate 100 ml of seed medium containing the following per liter of deionized water: soluble starch, 20 g; Dextrose, 5 g; N-Z case, 3 g; yeast extract, 2 g; fish meat extract, 5 g; calcium carbonate 3 g, in a 500-ml flask. The culture was incubated at 28° C. on a rotary shaker operating at 250 rpm for 3 days. Four ml of the resulting culture was added to each of six 500-ml flasks containing the 100 ml of fresh seed medium and the culture was incubated at 28° C. on a rotary shaker operating at 250 rpm for 3 days. The resulting culture from six flasks was pooled and 4 ml of the combined culture was used to inoculate each of eighty 500 ml flasks containing 100 ml of producing medium consisting of the following per liter of deionized water: HY yeast 412, 10 g; Dextrose, 20 g; Nutrisoy, 10 g. The producing cultures were incubated at 28° C. on a rotary shaker operating at 250 rpm for 27 hours. Five ml of 5-fluoro-dl-tryptophan aqueous solution (4 mg/ml, sterilized by passing through a 0.22 $\mu$m filter) was then added to each flask. The cultures were then returned to the shaker and incubated for an additional 42 hours at 28° C. and 250 rpm. The cultures were then processed for the recovery of the 5-fluoronocathiacin.

Example 2

From the frozen vegetative stock culture of Nocardia sp. ATCC-202099, 4 ml were used to inoculate 100 ml of seed medium containing the following per liter of deionized water: soluble starch, 20 g; Dextrose, 5 g; N-Z case, 3 g; yeast extract, 2 g; fish meat extract, 5 g; calcium carbonate 3 g, in a 500-ml flask. The culture was incubated at 28° C. on a rotary shaker operating at 250 rpm for 3 days. The resulting cultures from two flasks were pooled and 2 ml of the combined culture were used to inoculate each of ten 500-ml flasks containing the 100 m of producing medium consisting of the following per liter of deionized water: HY yeast 412, 10 g; Dextrose, 20 g; Nutrisoy, 10 g. The producing cultures were incubated at 28° C. on a rotary shaker operating at 250 rpm for 24 hours. Five ml of 5-fluoro-dl-tryptophan aqueous solution (4 mg/ml, sterilized by passing through a 0.22 $\mu$m filter) was then added to each flask. The cultures were then returned to the shaker and incubated for additional 4 days at 28° C. and 250 rpm. The cultures were then processed for the recovery of the 5-fluoronocathiacin.

Isolation

Example 3
Preparation of Crude Extract

Fermentation broth of Nocardia sp. ATCC-202099 (5 L.) was extracted (whole broth including mycelia) with approximately 2 L. ethyl acetate by vigorous shaking. The biphasic mixture was vacuum filtered through a pad of dicalite. The phases were separated and the lower, aqueous portion extracted one additional time with 2 L. ethyl acetate. The mycelia-Dicalite cake was soaked in 2 L. chloroform-methanol 1:1 for 1 hr. The pale yellow ethyl acetate and chloroform-methanol extracts were pooled and evaporated in vacuo to dryness in a rotary evaporator to yield approximately 740 mg of Residue A.

Silica Gel Vacuum Liquid Chromatography of Residue A

The crude extract containing nocathiacin antibiotics (Residue A) was preadsorbed onto 2 g Merck LiChroprep Silica Gel 60 (25–40µ) and applied to a 2.5×15 cm fritted filter funnel packed half full with this adsorbent. Elution using house vacuum was initially with chloroform (100 ml), followed by chloroform-methanol-water mixtures in a step gradient (e.g. $CHCl_3$—MeOH—$H_2O$ 98:2:0.2, 97:3:0.3 (2×), 95:5:0.5, 93:7:0.7, 90:10:1, v/v, 100 ml each. Fractions were consolidated on the basis of silica TLC profiles (chloroform-methanol-water 90:10:1 v/v, long wavelength UV and ceric sulfate spray). In this manner, 5-fluoronocathiacin was detected in the second $CHCl_3$—MeOH—$H_2O$ 97:3:0.3 fraction and the $CHCl_3$—MeOH—$H_2O$ 95:5:0.5 fraction. These fractions were combined and evaporated to dryness, (Residue B, 121 mg).

Isolation of 5-fluoronocathiacin

Residue B was further purified using the specified Beckman System Gold preparative HPLC system. A typical sample injection size was 25–50 mg/100–200 µl DMSO. Elution was isocratic using 0.1M ammonium acetate—tetrahydrofuran mixtures (e.g. 0.1M ammonium acetate—tetrahydrofuran 6:4, 55:45, 57:43, v/v). Elution flow rate was 10 ml/min. Detection (UV) was at 360 nm. In this manner, 5-fluoronocathiacin (18 mg total yield) was obtained.

Physico-Chemical Properties of 5-Fluoronocathiacin
Description: yellow amorphous solid
Molecular Formula: $C_{61}H_{59}FN_{14}O_{18}S_5$
Molecular Weight: 1454
Mass Spectrum: HR-ESIMS $[M+H]^+$ m/z 1455.281 ESI-MS/MS fragmentation ions: m/z 1284, 1266, 1240, 1222, 1204, 1172, 788
Infrared Spectrum: Major IR Bands ($cm^{-1}$) 3391, 2938, 1731, 1667, 1532, 1485, 1418, 1385, 1319, 1253, 1200, 1160, 1129, 1090, 1069, 1036, 1013, 885, 802, 755.
Ultraviolet Spectrum: $\lambda_{max}$ (MeOH) nm 220, 292, 361 (log ε 4.94, 4.60, 4.24).
Circular Dichroism: CD λ nm (Δε) (MeOH) 211 (+38.0), 236 (−47.3), 265 (+26.5), 307 (−8.7), 355 (+8.0).

| | |
|---|---|
| HPLC (Rt) | 26.9 min; (C18; Acetonitrile - 0.01 M potassium phosphate buffer pH 3.5 gradient (J. Chromatogr. 385, 99 (1987)). |
| $^1$H-NMR | Observed Chemical Shifts (relative to DMSO-$d_6$ signal δ 2.49): δ 10.08 (1H, s), 9.21 (1H, s), 8.66 (1H, d, J = 8.2 Hz), 8.64 (1H, s), 8.54 (1H, s), 8.53 (1H, s), 8.29 (1H, s), 8.11 (1H, s br), 7.87 (1H, s), 7.84 (1H, s), 7.78 (1H, dd, J = 4.5, 10.0 Hz), 7.66 (1H, s br), 7.33 (2H, m), 6.41 (1H, s), 5.81 (1H, d, J = 13.7 Hz), 5.77 (1H, s), 5.70 (1H, d, J = 8.4 Hz), 5.40 (1H, d, J = 12.9 Hz), 5.24 (1H, d br, J = 6.9 Hz), 4.97 (1H, d, J = 3.9 Hz), 4.78 (1H, d, J = 10.3 Hz), 4.59 (1H, d, J = 10.8 Hz), 4.37 (1H, d, J = 9.7 Hz), 4.28 (1H, m), 4.12 (1H, d, J = 10.5 Hz), 4.04 (1H, d, J = 9.4 Hz), 3.93 (3H, s), 3.79 (1H, d br, J = 6.8 Hz), 2.53 (6H, s), 2.34 (1H, m), 2.10 (1H, s br), 2.03 (3H, s), 1.98 (1H, m), 1.82 (1H, d, J = 14.2 Hz), 1.44 (3H, s), 1.18 (3H, d, J = 4.8 Hz), 0.59 (3H, d, J = 6.4 Hz). |
| $^{13}$C-NMR | Observed Chemical Shifts (relative to DMSO-$d_6$ signal δ 39.6): δ 172.0, 167.8, 167.6, 167.4, 166.5, 165.2, 164.1, 163.3, 161.7, 160.8, 160.6, 160.5, 158.8, 158.6, 154.9, 154.7, 149.9, 149.6, 148.7, 145.8, 141.6, 135.7, 134.5, 131.4, 130.0, 127.3, 127.2, 126.1, 125.6, 119.6, 113.6, 112.7, 111.4, 109.6, 103.7, 95.2, 79.1, 70.6, 68.4, 67.6, 66.2, 65.5, 64.1, 63.1, 58.5, 56.2, 55.3, 50.5, 50.2, 44.4, 40.4, 30.6, 18.0, 17.8, 13.1 |
| $^{19}$F-NMR | Observed Chemical Shifts (relative to $CCl_3F$ signal δ 0.0): δ -128.2 |

BIOLOGICAL EVALUATION OF 5-FLUORONOCATHIACIN

Example 4
Antibiotic Activity of 5-Fluoronocathiacin

To demonstrate its antimicrobial properties, the minimum inhibitory concentration (MIC) for 5-fluoronocathiacin antibiotic of the invention was obtained against a variety of bacteria using a conventional broth dilution assay (serial broth dilution method using nutrient broth (Difco)). The results obtained are shown in Table 1 below, and demonstrate that 5-fluoronocathiacin has utility in treating bacterial infections.

TABLE 1

| Organism | Strain # | MIC (µg/ml) 5-Fluoronocathiacin |
|---|---|---|
| Streptococcus pneumoniae | A9585 | ≦0.002 |
| Streptococcus pneumoniae/penicillin intermediate | A27881 | ≦0.002 |
| Streptococcus pneumoniae/penicillin resistant | A28272 | ≦0.002 |
| Enterococcus faecalis | A20688 | 0.25 |
| Enterococcus faecalis | A27519 | 0.25 |
| Enterococcus faecalis +50% calf serum | A20688 | 0.25 |
| Enterococcus faecium | A24885 | 0.25 |
| Enterococcus avium | A27456 | 0.25 |
| Staphylococcus aureus/β-lactamase positive | A15090 | 0.125 |
| Staphylococcus aureus + 50% calf serum | A15090 | 0.125 |
| Staphylococcus aureus/QC/ATCC #29213 | A24407 | 0.125 |
| Staphylococcus aureus/homo methicillin resistant | A27223 | 0.003 |
| Staphylococcus aureus + 50% calf serum | A27223 | 0.003 |
| Staphylococcus epidermidis | A24548 | 0.007 |
| Staphylococcus haemolyticus | A27298 | 0.003 |
| Moraxella catarrhalis/β-lactamase positive | A22344 | 0.06 |
| Moraxella catarrhalis/β-lactamase positive | A25409 | 0.06 |

6-FLUORONOCATHIACIN (R IS OH; X IS 6-FLUORO) PREPARED BY PRECURSOR-DIRECTED BIOSYNTHESIS

Biosynthesis

Example 5

Directed biosynthesis of 6-fluoronocathiacin

From the frozen vegetative stock culture of using Nocardia sp. ATCC 202099, 4 ml was used to inoculate 100 ml of seed medium contained the following per liter of deionized water: soluble starch, 20 g; Dextrose, 5 g; N-Z case, 3 g; yeast extract, 2 g; fish meat extract, 5 g; calcium carbonate 3 g, in a 500-ml flask. The culture was incubated at 28° C. on a rotary shaker operating at 250 rpm for 3 days. Four ml of the resulting culture was added to each of four 500-ml flasks containing the 100 ml of fresh seed medium and the culture was incubated at 28° C. on a rotary shaker operating at 250 rpm for 3 days. The resulting culture from four flasks was pooled and 4 ml of the combined culture was used to inoculate each of sixty 500-ml flasks containing 100 ml of producing medium consisting of the following per liter of deionized water: HY yeast 412, 10 g; Dextrose, 20 g; Nutrisoy, 10 g. The producing cultures were incubated at 28° C. on a rotary shaker operating at 250 rpm for 20 hours. Five ml of 6-fluoro-dl-tryptophan aqueous solution (4 mg/ml, sterilized by passing through a 0.22 $\mu$m filter) was then added to each flask. The cultures were then returned to the shaker and incubated for additional 27 hours at 28° C. and 250 rpm. The cultures were processed for the recovery of 6-fluoronocathiacin.

Isolation

Example 6

Preparation of Crude Extract

Fermentation broth of Nocardia sp. ATCC-202099 (6.5 L.) was extracted (whole broth including mycelia) with approximately 4 L. ethyl acetate. The biphasic mixture was vacuum filtered through a pad of dicalite. The phases were separated and the lower, aqueous portion extracted one additional time with 3 L. ethyl acetate. The mycelia-dicalite cake was extracted with 1.5 L. chloroform-methanol 1:1. The pale yellow ethyl acetate and chloroform-methanol extracts were pooled and evaporated in vacuo to dryness in a rotary evaporator to yield approximately 1.6 g of Residue C.

Silica Gel Vacuum Liquid Chromatography of Residue C

The crude extract containing nocathiacin antibiotics (Residue C) was preadsorbed onto 2 g Merck LiChroprep Silica Gel 60 (25–40$\mu$) and applied to a 2.5×15 cm fritted filter funnel packed two-thirds full with this adsorbent (13 g). Elution using house vacuum was initially with chloroform (100 ml), followed by chloroform-methanol-water mixtures in a step gradient (e.g. $CHCl_3$—MeOH—$H_2O$ 98:2:0.2, 97:3:0.3, 95:5:0.5 (2×), 93:7:0.7, v/v, 100 ml each. Fractions were consolidated on the basis of silica TLC profiles (chloroform-methanol-water 90:10:1 v/v, long wavelength UV and ceric sulfate spray). In this manner, 6-fluoronocathiacin was detected in the $CHCl_3$—MeOH—$H_2O$ 97:3:0.3 fraction and the first $CHCl_3$—MeOH—$H_2O$ 95:5:0.5 fraction. These fractions were combined and evaporated to dryness, (Residue D, 567 mg).

Isolation of 6-fluoronocathiacin

Residue D was further purified using the specified Beckman System Gold preparative HPLC system: YMC-Pack Pro C18 column (5$\mu$ particle size, 120 Å pore size, 20 mm i.d.×150 mm l.), fitted with a ODS-A 25$\mu$particle size, 120 Å pore size, 10 mm i.d.×10 mm l. drop-in guard module. A typical sample injection size was 50–100 mg/200–400 $\mu$l DMSO. Elution was isocratic using 0.1M ammonium acetate—tetrahydrofuran 6:4. Elution flow rate was 10 ml/min. Detection (UV) was at 360 nm. In this manner, 6-fluoronocathiacin (13 mg total yield) was obtained.

Physico-Chemical Properties of 6-Fluoronocathiacin

Description: yellow amorphous solid
Molecular Formula: $C_{61}H_{59}FN_{14}O_{18}S_5$
Molecular Weight: 1454
Mass Spectrum: HR-ESIMS $[M+H]^+$ m/z 1455.276 ESI-MS/MS fragmentation ions: m/z 1284, 1266, 1240, 1222, 1204, 1172, 788
Infrared Spectrum: Major IR Bands ($cm^{-1}$) 3392, 2955, 1743, 1717, 1667, 1534, 1479, 1368, 1321, 1254, 1204, 1172, 1092, 1015, 756.
Ultraviolet Spectrum: $\lambda_{max}$ (MeOH) nm 223, 291, 366 (log $\epsilon$ 4.96, 4.59,4.28).
Circular Dichroism: CD $\lambda$ nm ($\Delta\epsilon$) (MeOH) 211 (+39.6), 235 (−53.6), 262 (+31.8), 306 (−7.0), 350 (+7.1).

| | |
|---|---|
| HPLC (Rt) | 26.9 min; (C18; Acetonitrile - 0.01 M potassium phosphate buffer pH 3.5 gradient (J. Chromatogr. 385, 99 (1987)). |
| $^1$H-NMR | Observed Chemical Shifts (relative to DMSO-$d_6$ signal $\delta$ 2.49): $\delta$ 10.04 (1H, s), 9.14 (1H, s), 8.63 (1H, d, J = 8.2 Hz), 8.61 (1H, s), 8.50 (1H, s), 8.45 (1H, s), 8.25 (1H, s), 8.06 (1H, s br), 7.81 (1H, s br), 7.79 (1H, s), 7.70 (1H, s br), 7.63 (1H, s br), 7.46 (1H, d, J = 8.5 Hz), 7.29 (1H, d, J = 7.7 Hz), 7.12 (1H, d, J = 9.6 Hz), 6.33 (1H, s), 5.89 (1H, d, J = 12.1 Hz), 5.66 (1H, s), 5.60 (1H, d, J = 8.3 Hz), 5.14 (1H, m), 4.96 (1H, d, J = 12.5 Hz), 4.87 (1H, d, J = 3.5 Hz), 4.69 (1H, d, J = 10.0 Hz), 4.51 (1H, d, J = 10.5 Hz), 4.27 (1H, d, J = 9.7 Hz), 4.24 (1H, m), 4.01 (1H, d, J = 9.7 Hz), 3.95 (1H, d, J = 9.3 Hz), 3.85 (3H, s), 3.70 (1H, m), 2.49 (6H, s), 2.04 (1H, s br), 2.00 (3H, s), 1.94 (1H, m), 1.78 (1H, d, J = 13.8 Hz), 1.40 (3H, s), 1.15 (3H, d, J = 4.7 Hz), 0.56 (3H, d, T = 6.5 Hz). |
| $^{13}$C-NMR | Observed Chemical Shifts (relative to DMSO-$d_6$ signal $\delta$ 39.6): $\delta$ 171.8, 167.9, 167.4, 167.3, 165.9, 165.3, 164.5, 163.3, 161.7, 160.9, 160.6, 160.5, 160.3, 159.1, 158.7, 158.4, 155.3, 149.8, 149.3, 148.8, 145.8, 140.2, 136.3, 135.2, 134.4, 130.5, 129.9, 127.2, 127.0, 126.5, 125.9, 125.6, 119.2, 116.4, 112.5, 111.9, 109.6, 107.1, 103.4, 98.1, 95.2, 79.2, 70.6, 68.4, 67.7, 66.5, 66.3, 65.5, 64.1, 63.1, 56.3, 55.3, 50.5, 50.3, 44.5, 40.4, 30.6, 18.0, 17.9, 13.1 |
| $^{19}$F-NMR | Observed Chemical Shifts (relative to $CCl_3F$ signal $\delta$ 0.0): $\delta$ -118.0 |

BIOLOGICAL EVALUATION OF 6-FLUORONOCATHIACIN

Example 7

Antibiotic Activity of 6-Fluoronocathiacin

To demonstrate its antimicrobial properties, the minimum inhibitory concentration (MIC) for 6-fluoronocathiacin antibiotic of the invention was obtained against a variety of bacteria using a conventional broth dilution assay (serial broth dilution method using nutrient broth (Difco)). The results obtained are shown in Table 2 below, and demonstrate that 6-fluoronocathiacin has utility in treating bacterial infections.

TABLE 2

| Organism | Strain # | MIC (µg/ml) 6-Fluoronocathiacin |
|---|---|---|
| Streptococcus pneumoniae | A9585 | <0.0005 |
| Streptococcus pneumoniae/penicillin intermediate | A27881 | <0.0005 |
| Streptococcus pneumoniae/penicillin resistant | A28272 | <0.0005 |
| Enterococcus faecalis | A20688 | <0.001 |
| Enterococcus faecalis +50% calf serum | A20688 | 0.015 |
| Enterococcus faecium | A24885 | 0.004 |
| Staphylococcus aureus/β-lactamase positive | A15090 | 0.002 |
| Staphylococcus aureus + 50% calf serum | A15090 | 0.015 |
| Staphylococcus aureus/QC/ATCC #29213 | A24407 | 0.002 |
| Staphylococcus aureus/homo methicillin resistant | A27223 | 0.002 |
| Staphylococcus aureus + 50% calf serum | A27223 | 0.015 |
| Staphylococcus epidermidis | A24548 | 0.004 |
| Staphylococcus haemolyticus | A27298 | 0.004 |
| Moraxella catarrhalis/β-lactamase positive | A22344 | 0.25 |
| Haemophilus influenzae/β-lactamase negative | A20191 | >16 |
| Haemophilus influenzae/β-lactamase positive | A21515 | >16 |
| Staphylococcus aureus/209P/ATCC #6538P | A9497 | 0.002 |
| Staphylococcus aureus/Thiostrep. Res/Mutant | A9497 | 16 |
| Bacillus subtilis/ATCC #6633 | A9506A | 0.002 |
| Bacillus subtilis/ Thiostrep. Res/Mutant | A9506A | >32 |

We claim:

1. A halogen- or hydroxy-substituted nocathiacin compound, or a pharmaceutically-acceptable salt thereof, of the formula

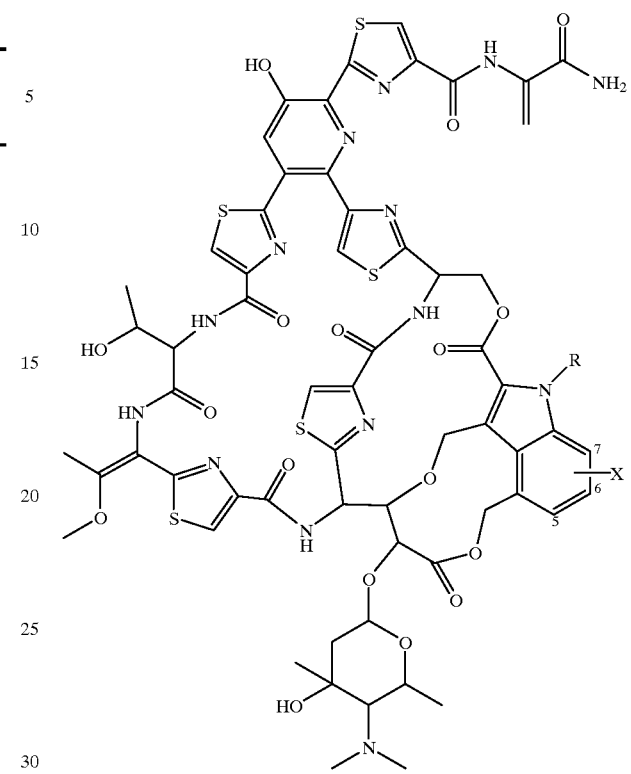

wherein:
R is H or OH and
X is halogen or OH.

Figure 2:
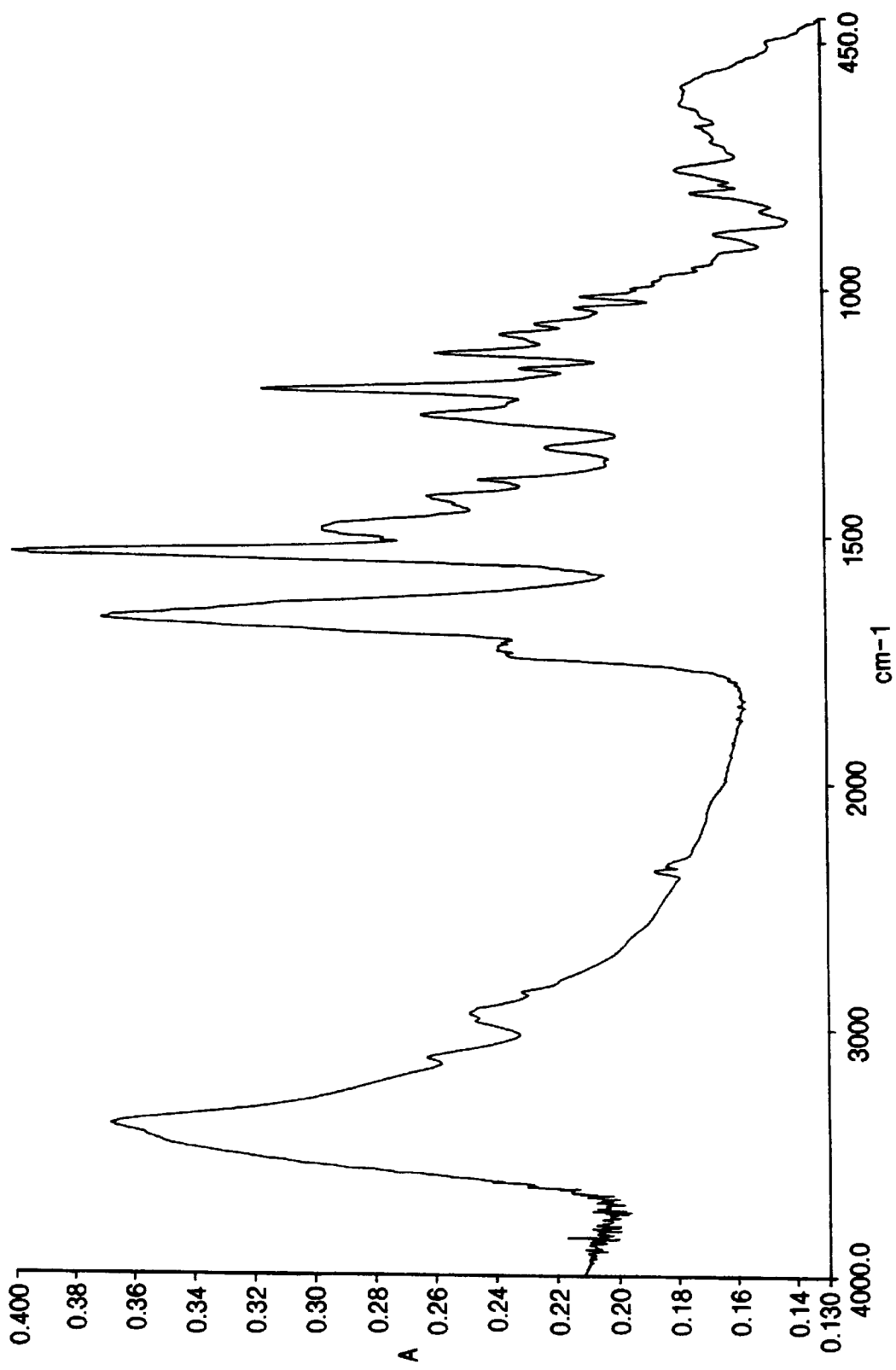
FIG. 2 Shows the infrared absorption (IR) spectrum of 5-fluoronocathiacin.
Figure 3:
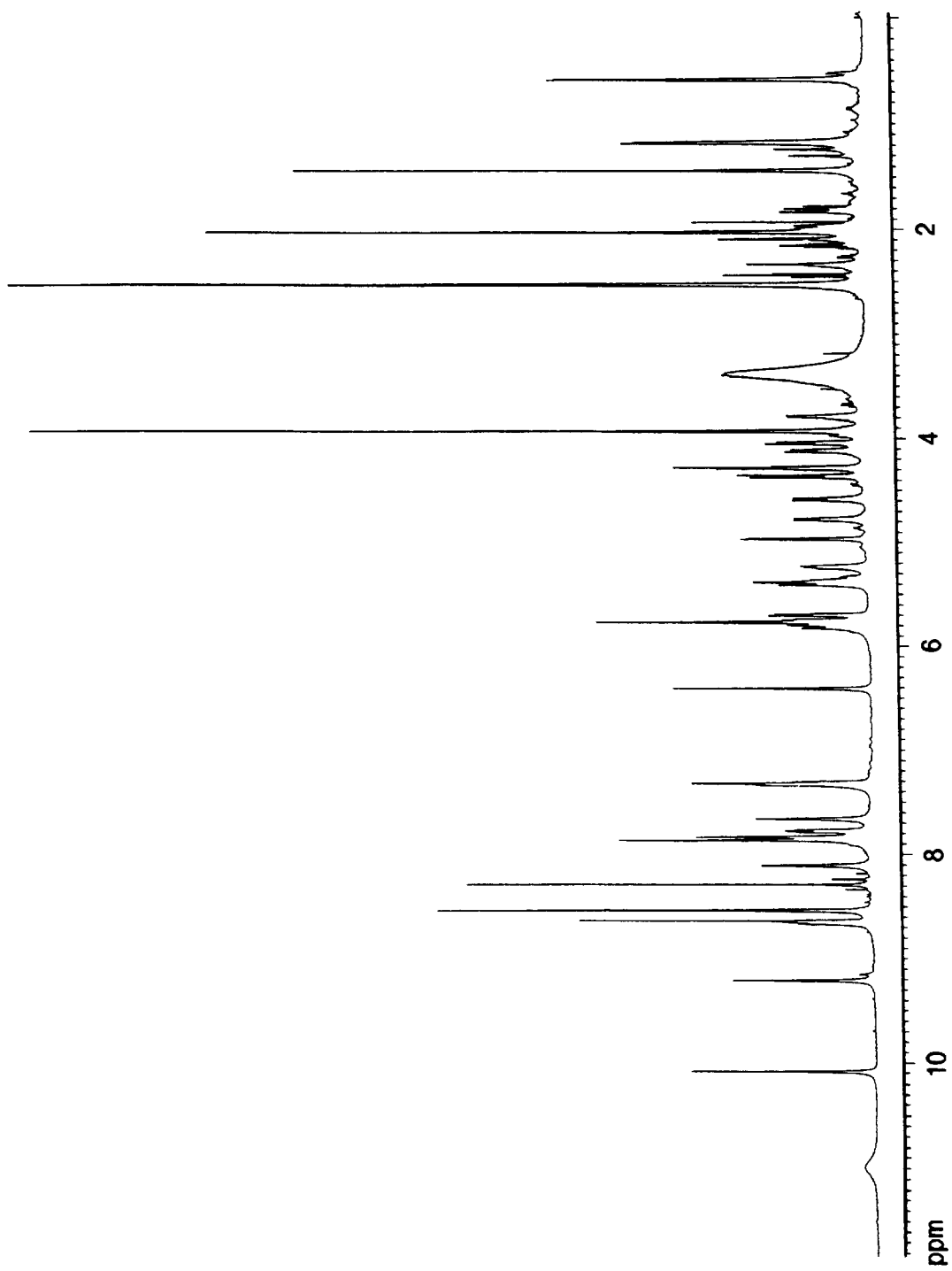
FIG. 3 Shows the $^1$H-NMR spectrum (500 MHz) of 5-fluoronocathiacin in deuterated dimethylsulfoxide.
Figure 4:
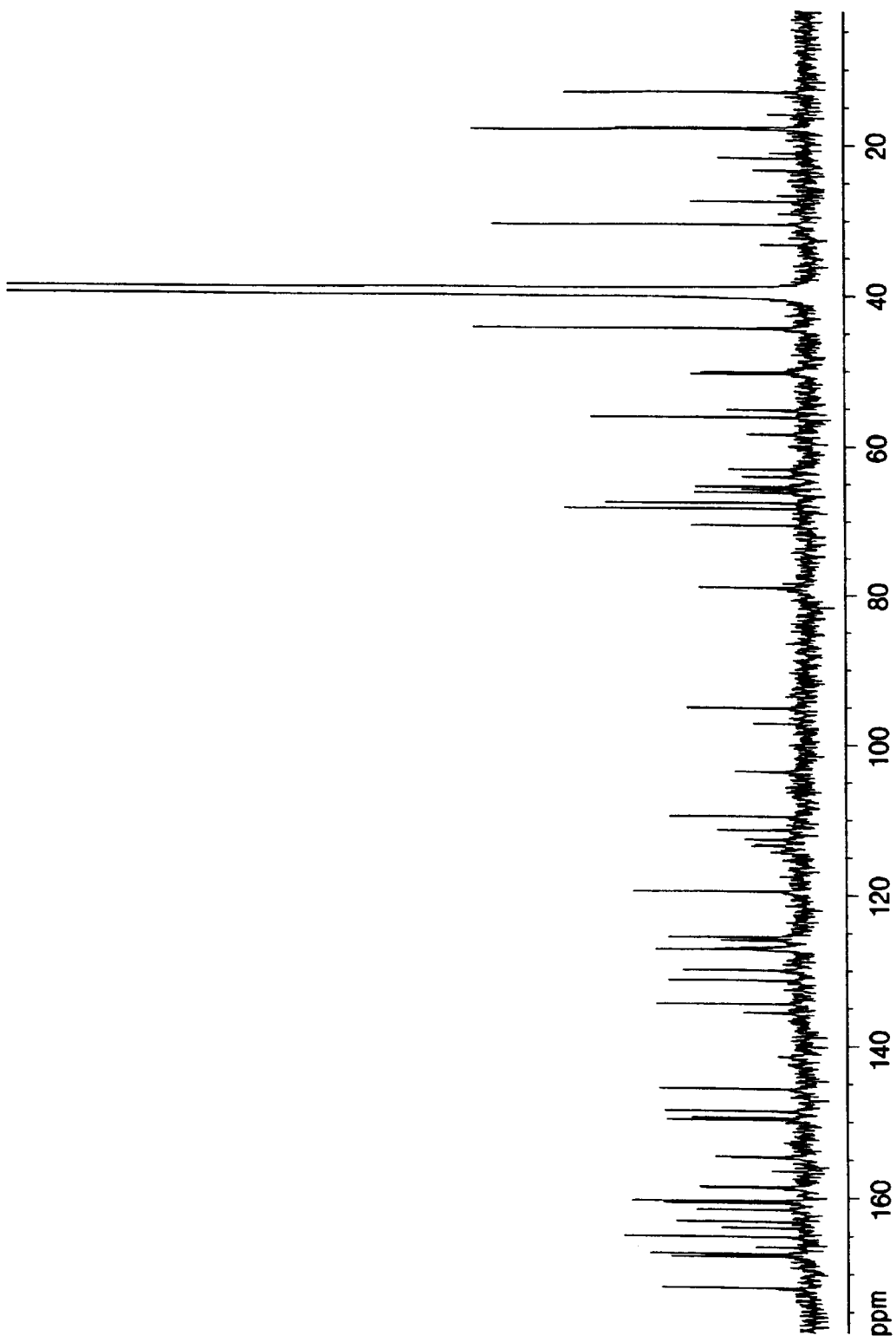
FIG. 4 Shows the $^{13}$C-NMR (125 MHz) spectrum of 5-fluoronocathiacin in deuterated dimethylsulfoxide.

2. The compound of claim 1 wherein R is OH and X is 5-fluoro, having the following properties:
   (a) is a yellow colored amorphous solid;
   (b) has a molecular weight of 1454 as determined by mass spectrometry;
   (c) has the molecular formula $C_{61}H_{59}FN_{14}O_{18}S_5$;
   (d) exhibits an ultraviolet absorption spectrum when dissolved in methanol substantially as shown in FIG. 1;
   (e) exhibits an infrared absorption spectrum (KBr) substantially as shown in FIG. 2;
   (f) when dissolved in deuterated dimethylsulfoxide exhibits a proton magnetic resonance spectrum substantially as shown in FIG. 3;
   (g) when dissolved in deuterated dimethylsulfoxide exhibits a $^{13}C$ magnetic resonance spectrum substantially as shown in FIG. 4;
   (h) exhibits a high performance liquid chromatography retention time of 26.9 minutes with a C18 reversed phase silica gel column using a 0.01M potassium phosphate buffer pH 3.5—acetonitrile gradient.

Figure 5:
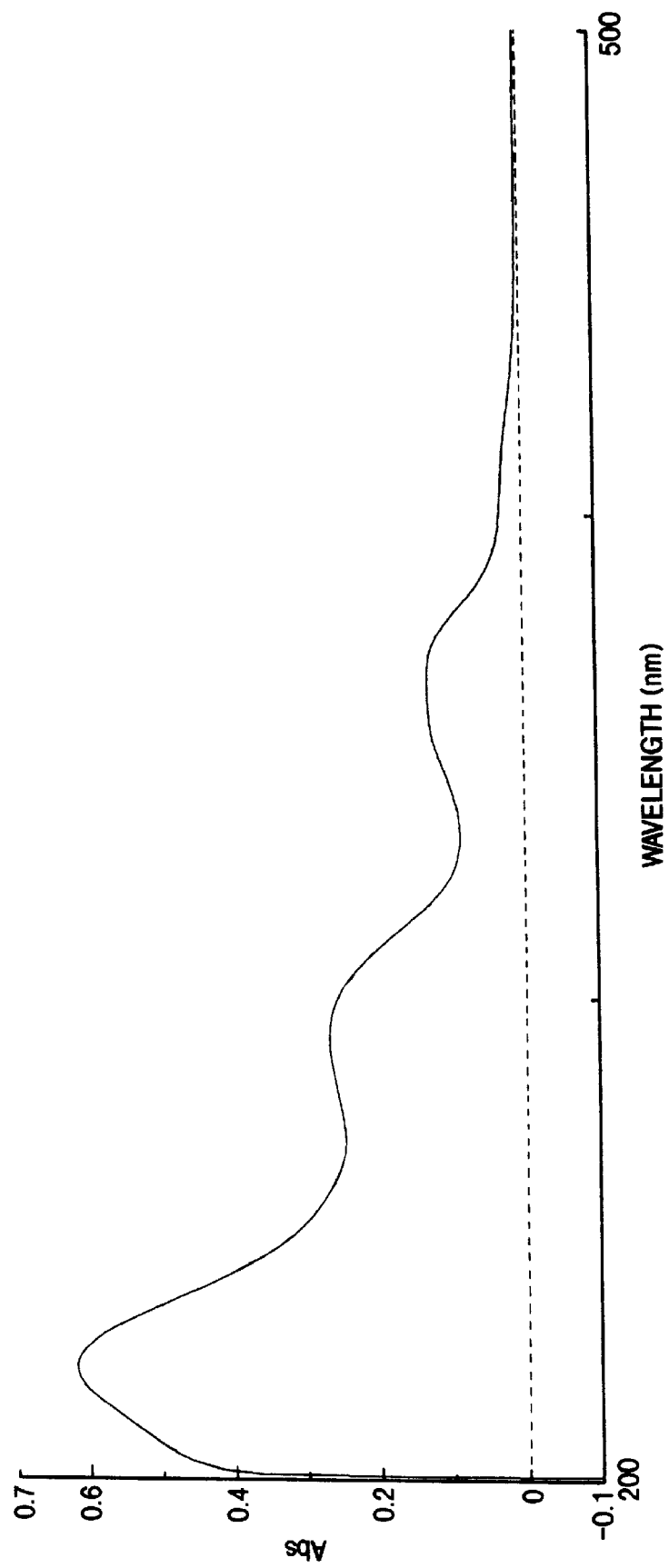
FIG. 5 Shows the ultraviolet absorption (UV) spectrum of 6-fluoronocathiacin.
Figure 6:
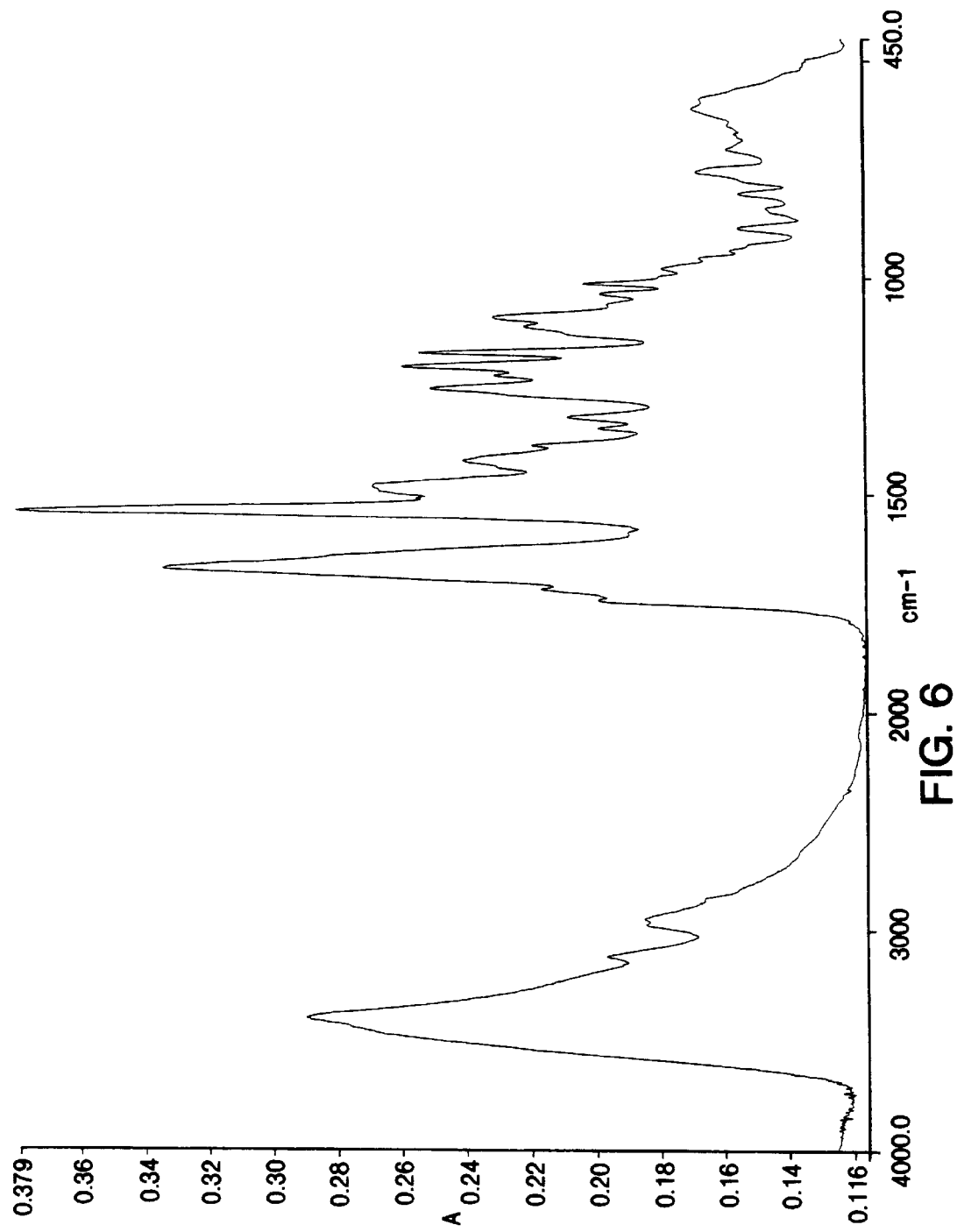
FIG. 6 Shows the infrared (IR) spectrum of 6-fluoronocathiacin.
Figure 7:
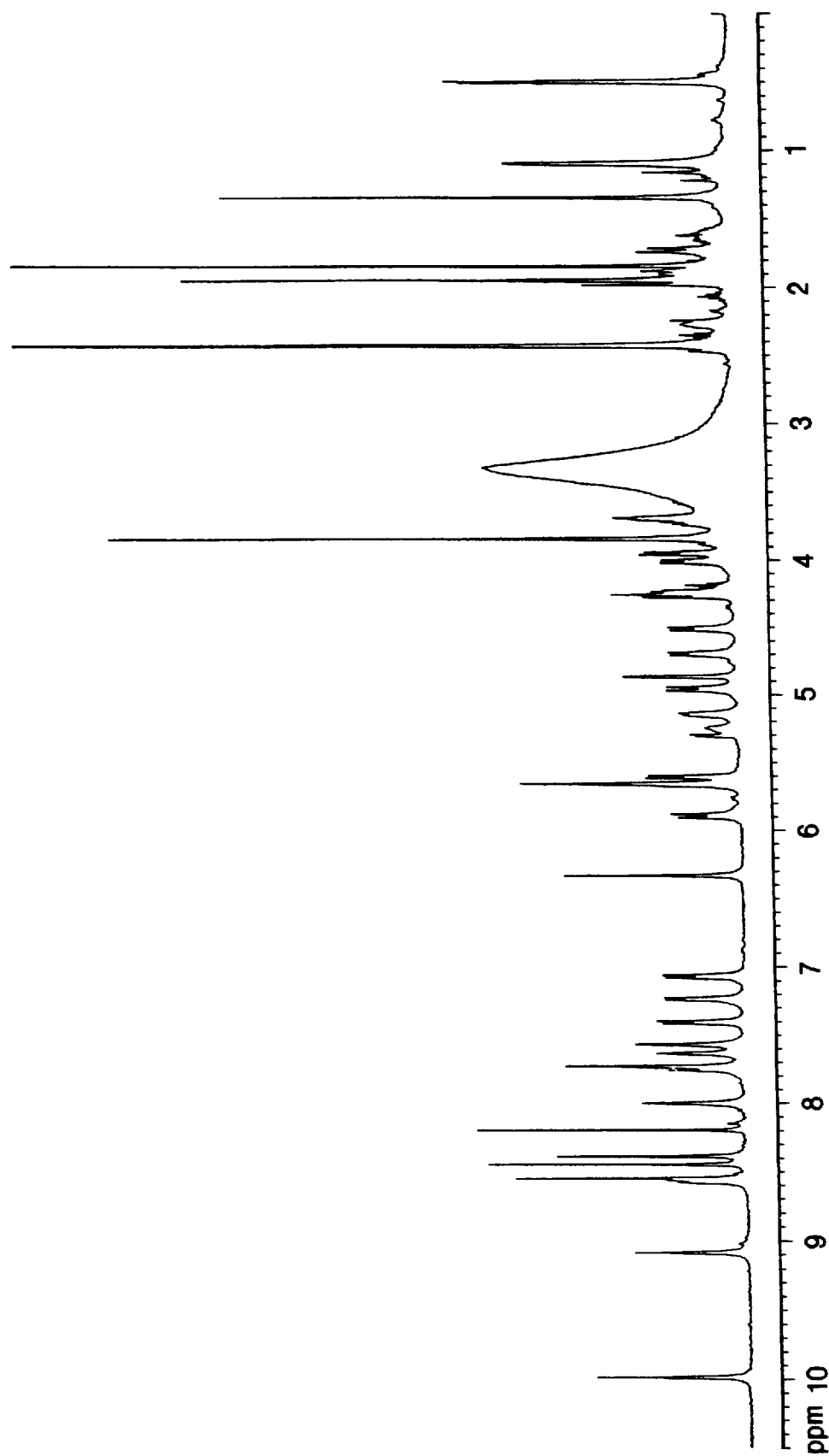
FIG. 7 Shows the $^1$H-NMR spectrum (500 MHz) of 6-fluoronocathiacin in deuterated dimethylsulfoxide.
Figure 8:
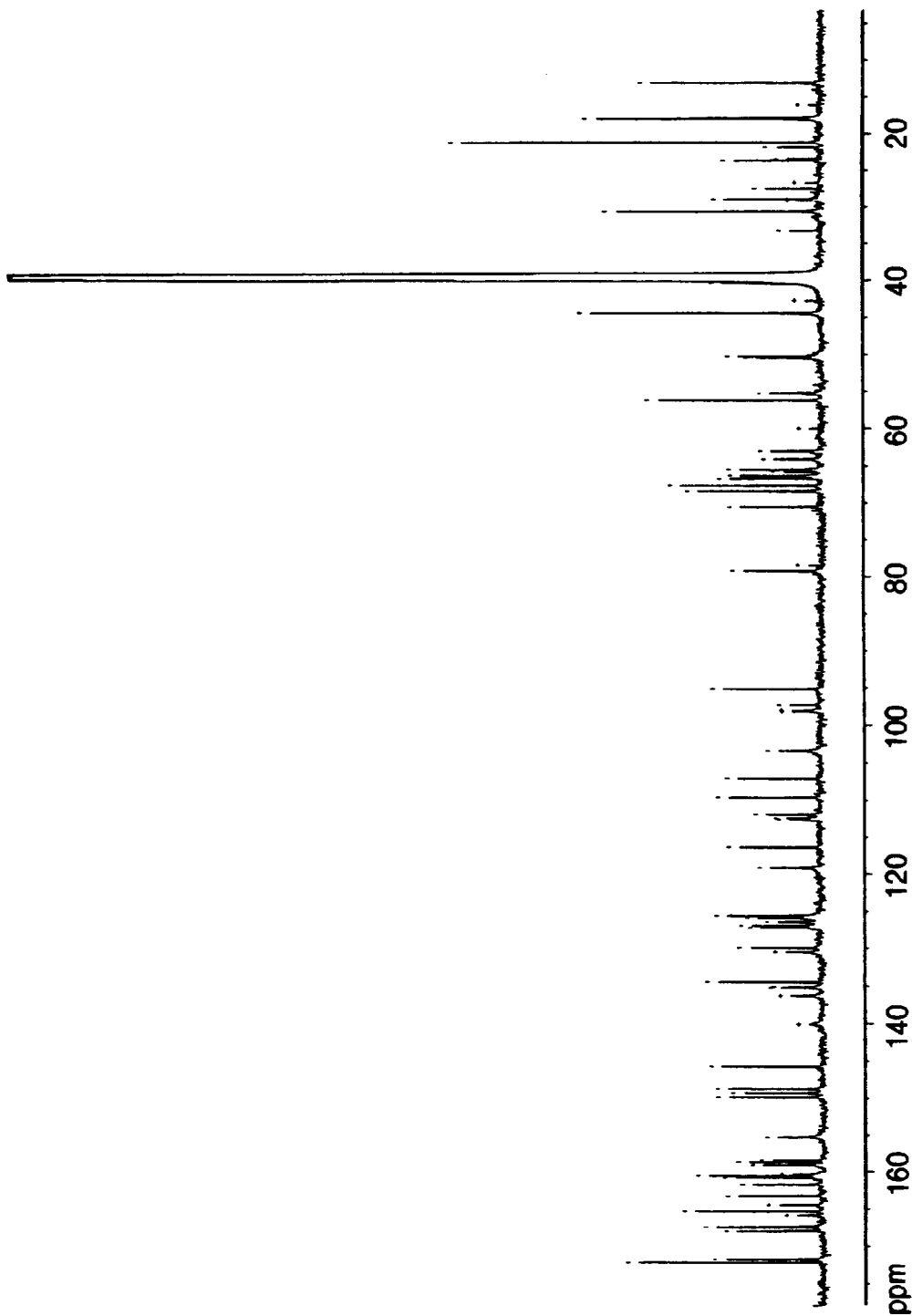
FIG. 8 Shows the $^{13}$C-NMR (125 MHz) spectrum of 6-fluoronocathiacin in deuterated dimethylsulfoxide.

3. The compound of claim 1 wherein R is OH and X is 6-fluoro, having the following characteristics:
   (a) is a yellow colored amorphous solid;
   (b) has a molecular weight of 1454 as determined by mass spectrometry;
   (c) has the molecular formula $C_{61}H_{59}FN_{14}O_{18}S_5$;
   (d) exhibits an ultraviolet absorption spectrum when dissolved in methanol substantially as shown in FIG. 5;
   (e) exhibits an infrared absorption spectrum (KBr) substantially as shown in FIG. 6;

(f) when dissolved in deuterated dimethylsulfoxide exhibits a proton magnetic resonance spectrum substantially as shown in FIG. 7;

(g) when dissolved in deuterated dimethylsulfoxide exhibits a $^{13}$C magnetic resonance spectrum substantially as shown in FIG. 8;

(h) exhibits a high performance liquid chromatography retention time of 26.9 minutes with a C18 reversed phase silica gel column using a 0.01M potassium phosphate buffer pH 3.5—acetonitrile gradient.

4. A pharmaceutical composition comprising a therapeutically effective amount of a compound as claimed in any of claims 1–3 and a pharmaceutically acceptable carrier or diluent.

5. A method for treating a bacterial infection of a mammal in need thereof comprising the step of administering a therapeutically effective amount of the pharmaceutical composition of claim 4 to said mammal.

6. A process for making a halogen- or hydroxy-substituted nocathiacin compound as claimed in any of claims 1–3 which comprises cultivating a nocathiacin-producing strain of Nocardia sp. in an aqueous nutrient medium in the presence of an appropriately substituted halogen- or hydroxy-tryptophan analog, until a recoverable amount of the desired substituted nocathiacin compound is produced by said organism in said culture medium and recovering the halogen or hydroxy substituted nocathiacin compound from the culture medium in a substantially pure form.

7. The process of claim 6 wherein the nocathiacin-producing strain is Nocardia sp. ATCC-202099.

\* \* \* \* \*